(12) United States Patent
Huseman

(10) Patent No.: US 8,454,600 B2
(45) Date of Patent: *Jun. 4, 2013

(54) TWO PIECE TUBE FOR SUCTION COAGULATOR

(75) Inventor: Mark J. Huseman, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 930 days.

This patent is subject to a terminal disclaimer.

(21) Appl. No.: 12/388,204

(22) Filed: Feb. 18, 2009

(65) Prior Publication Data

US 2010/0211068 A1     Aug. 19, 2010

(51) Int. Cl.
*A61B 18/18* (2006.01)

(52) U.S. Cl.
USPC .......................................................... 606/50

(58) Field of Classification Search
USPC ................ 606/49, 45, 23, 24, 27–29, 38, 40, 606/48, 32, 50
See application file for complete search history.

(56) References Cited

U.S. PATENT DOCUMENTS

| | | |
|---|---|---|
| 4,932,952 A | 6/1990 | Wojciechowicz, Jr. |
| 5,133,714 A | 7/1992 | Beane |
| 5,324,283 A | 6/1994 | Heckele |
| 5,520,685 A | 5/1996 | Wojciechowicz |
| 5,693,044 A | 12/1997 | Cosmescu |
| 5,730,742 A | 3/1998 | Wojciechowicz |
| 5,836,944 A | 11/1998 | Cosmescu |
| 5,925,045 A | 7/1999 | Reimels et al. |
| 5,968,042 A | 10/1999 | Ernster |
| 5,972,416 A | 10/1999 | Reimels et al. |
| 5,989,249 A | 11/1999 | Kirwan, Jr. |
| 6,149,648 A | 11/2000 | Cosmescu |
| 6,264,650 B1 | 7/2001 | Hovda et al. |
| 6,379,350 B1 | 4/2002 | Sharkey et al. |
| 6,406,476 B1 * | 6/2002 | Kirwan et al. ................. 606/50 |
| 6,458,125 B1 | 10/2002 | Cosmescu |

(Continued)

FOREIGN PATENT DOCUMENTS

| | | |
|---|---|---|
| DE | 2460481 | 12/1974 |
| DE | 2429021 | 1/1976 |

(Continued)

OTHER PUBLICATIONS

European Search Report EP 10153960 dated Sep. 7, 2010.

(Continued)

*Primary Examiner* — Nicholas Lucchesi
*Assistant Examiner* — Pritesh Patel

(57) ABSTRACT

An electrosurgical suction coagulator includes a housing having proximal and distal ends and a malleable elongated tube-like shaft extending longitudinally from the distal end of the housing. The tube-like shaft includes a tube-like dielectric sheath and a tube-like electrode having a first thermal conductivity $K_1$ disposed coaxially through the tube-like dielectric sheath. The tube-like electrode operably couples to a source of electrosurgical energy. A distal end of the tube-like electrode protrudes from a distal end of the tube-like shaft. One or more aspiration ports are defined in a distal end of the tube-like electrode. A proximal end of the tube-like electrode operably couples to a source of suction. A thermally conductive member having a second thermal conductivity $K_2$ that is less than $K_1$ is disposed concentrically about the tube-like shaft. The thermally conductive member is configured to impede the propagation of thermal energy in a proximal direction.

15 Claims, 6 Drawing Sheets

U.S. PATENT DOCUMENTS

| | | | |
|---|---|---|---|
| 6,458,126 B1 | 10/2002 | Doyle | |
| 6,595,990 B1 | 7/2003 | Weinstein et al. | |
| 7,537,594 B2 | 5/2009 | Sartor | |
| 2002/0049438 A1 | 4/2002 | Sharkey et al. | |
| 2003/0181904 A1 | 9/2003 | Levine et al. | |
| 2004/0193150 A1 | 9/2004 | Sharkey et al. | |
| 2004/0260280 A1 | 12/2004 | Sartor | |
| 2006/0235377 A1 | 10/2006 | Earley et al. | |
| 2008/0161791 A1 | 7/2008 | Cao et al. | |
| 2010/0211067 A1* | 8/2010 | Huseman | 606/49 |
| 2010/0211068 A1* | 8/2010 | Huseman | 606/49 |
| 2010/0211069 A1* | 8/2010 | Huseman | 606/49 |

FOREIGN PATENT DOCUMENTS

| | | |
|---|---|---|
| DE | 3045996 | 7/1982 |
| DE | 3710489 | 11/1987 |
| DE | 4139029 | 6/1993 |
| DE | 4326037 | 2/1995 |
| DE | 9117019.2 | 4/1995 |
| DE | 19537897 | 3/1997 |
| DE | 9117299 | 4/2000 |
| DE | 19848784 | 5/2000 |
| DE | 29724247 | 8/2000 |
| EP | 0186369 | 7/1986 |
| EP | 0447121 | 9/1991 |
| EP | 0612535 | 8/1994 |
| EP | 0956827 | 11/1999 |
| EP | 1050279 | 8/2000 |
| EP | 1050277 | 11/2000 |
| EP | 1082945 | 3/2001 |
| EP | 1090597 | 4/2001 |
| EP | 1090599 | 4/2001 |
| EP | 1127551 | 8/2001 |
| EP | 1199037 A2 | 4/2002 |
| EP | 1199038 A2 | 4/2002 |
| EP | 1293171 | 3/2003 |
| EP | 1199037 A3 | 7/2003 |
| EP | 1199038 A3 | 7/2003 |
| EP | 1323384 A2 | 7/2003 |
| EP | 1323384 A3 | 1/2004 |
| EP | 1561430 | 8/2005 |
| EP | 1090598 | 9/2005 |
| EP | 1570798 | 9/2005 |
| EP | 1595507 | 11/2005 |
| EP | 1656900 | 5/2006 |
| EP | 1645234 | 12/2006 |
| EP | 1602337 | 12/2007 |
| FR | 1340509 | 9/1963 |
| FR | 2235669 | 1/1975 |
| GB | 1014995 | 12/1965 |
| GB | 1222243 | 2/1998 |
| JP | 61-159953 | 7/1986 |
| SU | 1438745 | 11/1988 |
| WO | 91/13593 | 9/1991 |
| WO | 93/03678 | 3/1993 |
| WO | 94/20032 | 9/1994 |
| WO | 96/27337 | 9/1996 |
| WO | 96/39086 | 12/1996 |
| WO | 97/11647 | 4/1997 |
| WO | 98/43264 | 10/1998 |
| WO | 99/015091 | 4/1999 |
| WO | 01/62333 | 8/2001 |
| WO | 01/64122 | 9/2001 |
| WO | 02/47568 | 6/2002 |
| WO | 02/058762 | 8/2002 |
| WO | WO 03061499 | 7/2003 |
| WO | 2004/010883 | 2/2004 |
| WO | 2004/045436 | 6/2004 |
| WO | 2004/073753 | 9/2004 |
| WO | 2005/016142 | 2/2005 |
| WO | 2005/060849 | 7/2005 |

OTHER PUBLICATIONS

Grund et al., "Endoscopic Argon Plasma . . . Flexible Endoscopy" Surgery and Allied Technologies, No. 1, vol. 2, pp. 42-46 (Feb. 1994).
Farin et al. "Technology of Argon Plasma . . . Endoscopic Applications" Endoscopic Surgery and Allied Technologies, No. 1, vol. 2, pp. 71-77 (Feb. 1994).
Brand et al. "Electrosurgical Debulking of Ovarian Cancer: A New Technique Using the Argon Beam Coagulator" Gynecologic Oncology 39.
Hernandez et al. "A Controlled Study of the Argon Beam Coagulator for Partial Nephrectomy" The Journal of Urology, vol. 143, May (J.Urol. 143: 1062-1065, 1990).
Ward et al. "A Significant New Contribution to Radical Head and Neck Surgery" Arch Otolaryngol Head Neck Surg., vol. 115, Aug. 1989 pp. 921-923.
Mark H. Mellow, "The Role of Endoscopic Laser Therapy in Gastrointestinal Neoplasms" Advanced Therapeutic Endoscopy, pp. 17-21.
Silverstein et al., "Thermal Coagulation Therapy for Upper Gastrointestinal Bleeding" Advanced Therapeutic Endoscopy, pp. 79-84.
Waye et al., "Techniques in Therapeutic Endoscopy", W.B.Saunders Company, Philadelphia, PA., pp. 1.7-1.15.
European Search Report for 01102843.-2305 dated May 15, 2001.
International Search Report PCT/US98/19284, dated Jan. 14, 1999.
European Search Report for EP 05002257.3 dated Jun. 1, 2005.
International Search Report for EP 06019572 dated Nov. 21, 2006.
European Search Report EP 07 00 4356 dated Jul. 2, 2007.
European Search Report EP 07 00 4659 dated Mar. 5, 2008.
European Search Report EP 00 12 1241 dated Jan. 17, 2001.
Valleylab in the OR; Tonsillectomy Article; Aug. 2005.
Valleylab Suction Coagulators; May 2009.
International Search Report from PCT-US03-37111 dated Jul. 21, 2004.
International Search Report from PCT-US04-04685 dated Aug. 6, 2004.
International Search Report from EP-0401-5980 dated Sep. 30, 2004.
International Search Report from PCT-US03-22900 dated Nov. 20, 2003.
International Search Report from EP 05019882.9 dated Feb. 16, 2006.
International Search Report from EP 05021777.7 dated Feb. 23, 2006.
International Search Report from EP 06014461.5 dated Oct. 31, 2006.
International Search Report from EP 07009028 dated Jul. 16, 2007.
International Search Report from EP 06 00 5540 dated Sep. 24, 2007.
International Search Report from EP 08 00 2357 dated Jun. 30, 2008.

* cited by examiner

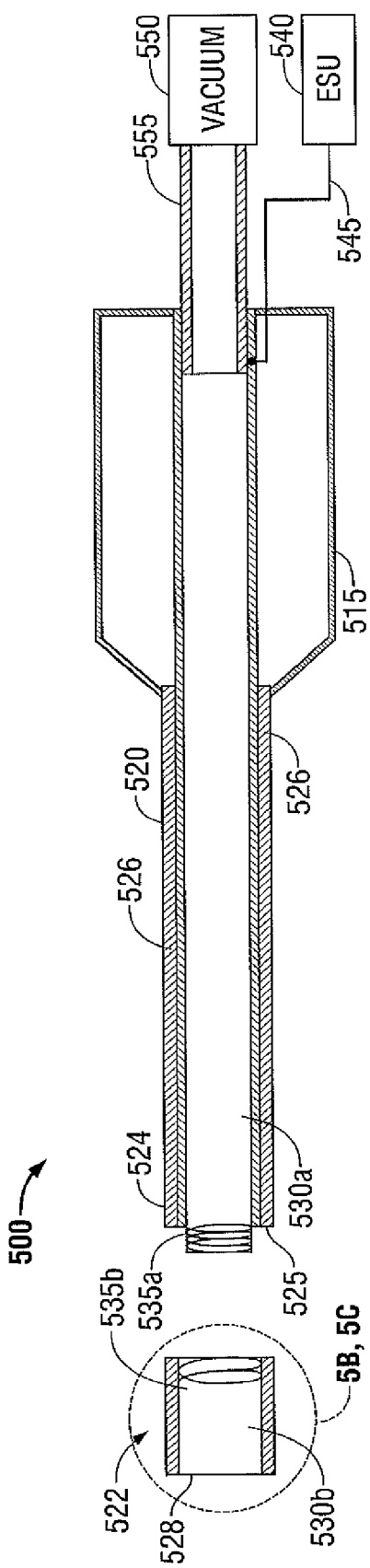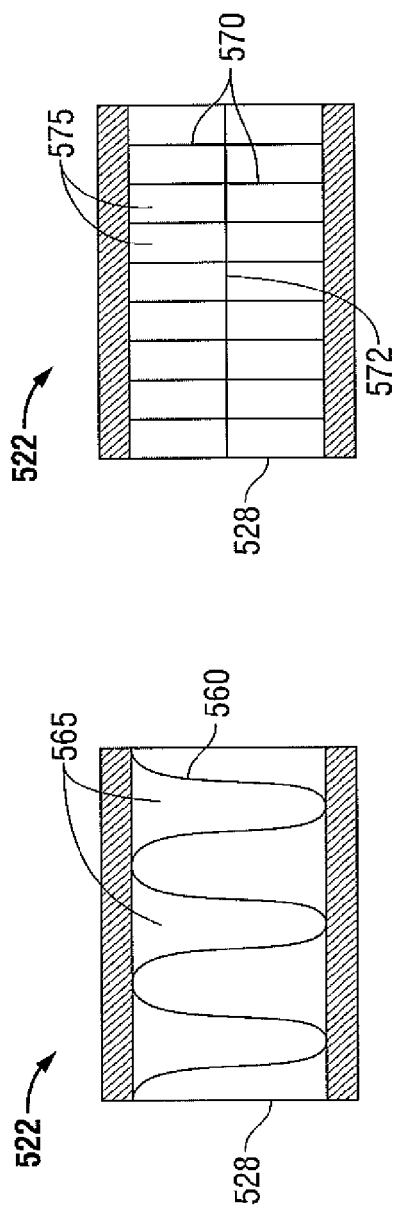
FIG. 5A
FIG. 5B
FIG. 5C

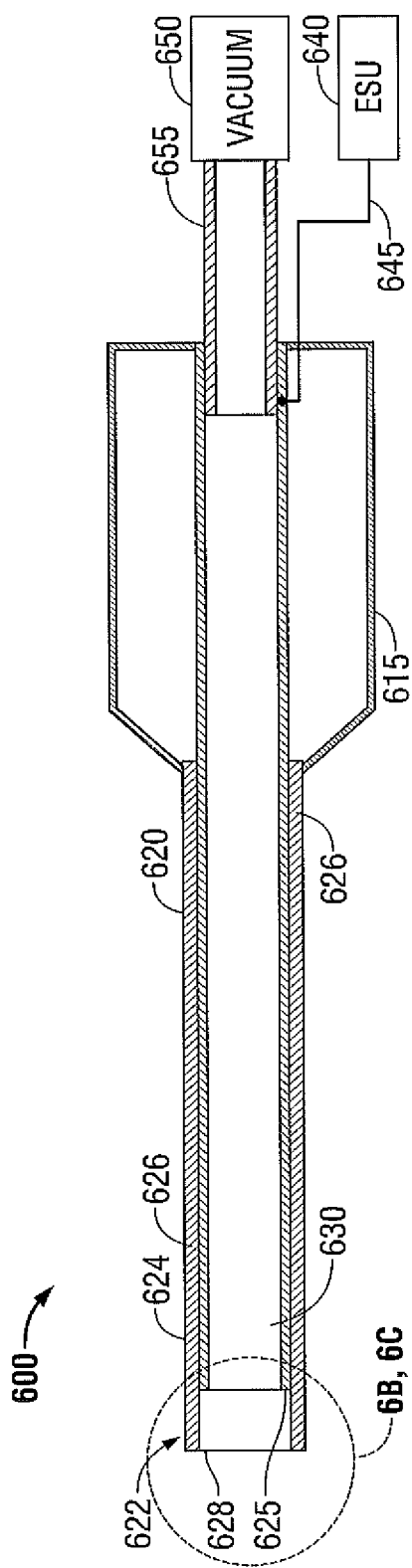
FIG. 6A
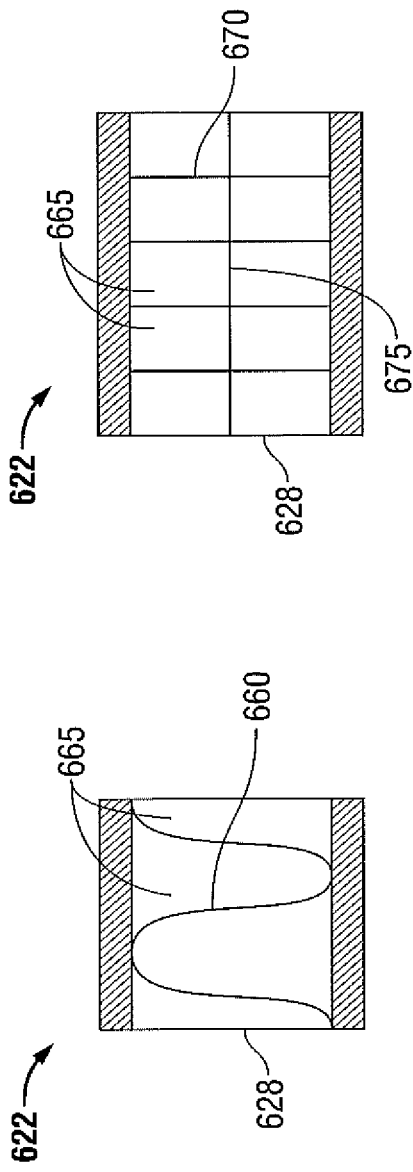
FIG. 6B
FIG. 6C

TWO PIECE TUBE FOR SUCTION COAGULATOR

BACKGROUND

1. Technical Field

The present invention relates generally to electrosurgical coagulators and, more particularly, to an electrosurgical suction coagulator having improved thermal insulation between the active electrode and adjacent tissue.

2. Background of Related Art

The coagulation of bleeding blood vessels and tissue using electrically conductive suction tubes is a technique which has been widely used for some time. Typically, a combination electrosurgery and suction device is employed in surgery wherever excessive blood must be removed from the bleeding site in order to facilitate hemostasis of any bleeding vessels.

Electrosurgical suction coagulators which both coagulate and dissect tissue have also been available for some time. Generally, these devices include a shaft formed from a conductive suction tube electrode having an electrically insulating coating over all but a most distal portion of the tube, so that the distal portion forms a generally annular ablating electrode. The shaft may be formed of malleable materials to enable a surgeon to bend the shaft to a desired shape. The distal end can be used as a blunt dissection device and/or a blunt coagulator. A suction source is attached to a proximal portion of the tube for evacuating excess fluid and debris from the surgical site through the distal end of the tube. The electrode is operably coupled to a source of electrosurgical energy, such as an electrosurgical generator.

The described electrosurgical suction coagulators may have drawbacks. In particular, heat conducted from the suction tube electrode to the outer surface of the shaft may cause the surface of the shaft to reach temperatures of 60° C. or greater. This may be a concern during surgical procedures, such as an electrosurgical adenotonsillectomy, where the shaft of a suction coagulator may be in proximity to, or in contact with, anatomical structures unrelated to the procedure, such as the uvula or the oral commissure. The elevated shaft temperature may have undesirable effects on such unrelated anatomical structures, including uvular edema and erythema of the oral commissure area.

SUMMARY

According to an embodiment of the present disclosure, an electrosurgical suction coagulator includes a housing having proximal and distal ends and a malleable elongated tube-like shaft extending longitudinally from the distal end of the housing. The tube-like shaft includes a tube-like dielectric sheath and a tube-like electrode having a first thermal conductivity $K_1$ disposed coaxially through the tube-like dielectric sheath. The tube-like electrode operably couples to a source of electrosurgical energy. A distal end of the tube-like electrode protrudes from a distal end of the tube-like shaft. One or more aspiration ports are defined in a distal end of the tube-like electrode. A proximal end of the tube-like electrode operably couples to a source of suction. A thermally conductive member having a second thermal conductivity $K_2$ that is less than $K_1$ is disposed concentrically about the tube-like shaft. The thermally conductive member is configured to impede the propagation of thermal energy in a proximal direction.

According to another embodiment of the present disclosure, an electrosurgical suction coagulator includes a housing having proximal and distal ends and a substantially malleable elongated tube-like shaft extending longitudinally from the distal end of the housing. The elongated tube-like shaft includes a tube-like dielectric sheath and a tube-like electrode disposed coaxially through the tube-like dielectric sheath. The tube-like electrode is configured to operably couple to a source of electrosurgical energy. The tube-like electrode protrudes at least partially from a distal end of the tube-like shaft. One or more aspiration ports are defined in a distal end of the tube-like electrode. A proximal end of the tube-like electrode is adapted to operably couple to a source of suction. A recess is defined concentrically in the tube-like shaft and is configured to receive a thermally conductive member therein. The thermally conductive member is adapted to impede the propagation of thermal energy proximally from the distal end of the tube-like shaft.

BRIEF DESCRIPTION OF THE DRAWINGS

The above and other aspects, features, and advantages of the present disclosure will become more apparent in light of the following detailed description when taken in conjunction with the accompanying drawings in which:

FIG. 5A is a side cutaway view of an embodiment of an electrosurgical suction coagulator in accordance with the present disclosure;

FIG. 5B is a side cutaway view of a component of the electrosurgical coagulator of FIG. 5A in accordance with another embodiment of the present disclosure;

FIG. 5C is a side cutaway view of a component of the electrosurgical coagulator of FIG. 5A in accordance with another embodiment of the present disclosure;

FIG. 6A is a side cutaway view of an embodiment of an electrosurgical suction coagulator in accordance with the present disclosure;

FIG. 6B is a side cutaway view of a component of the electrosurgical coagulator of FIG. 6A in accordance with another embodiment of the present disclosure; and FIG. 6C is a side cutaway view of a component of the electrosurgical coagulator of FIG. 6A in accordance with another embodiment of the present disclosure.

DETAILED DESCRIPTION

Figure 1:
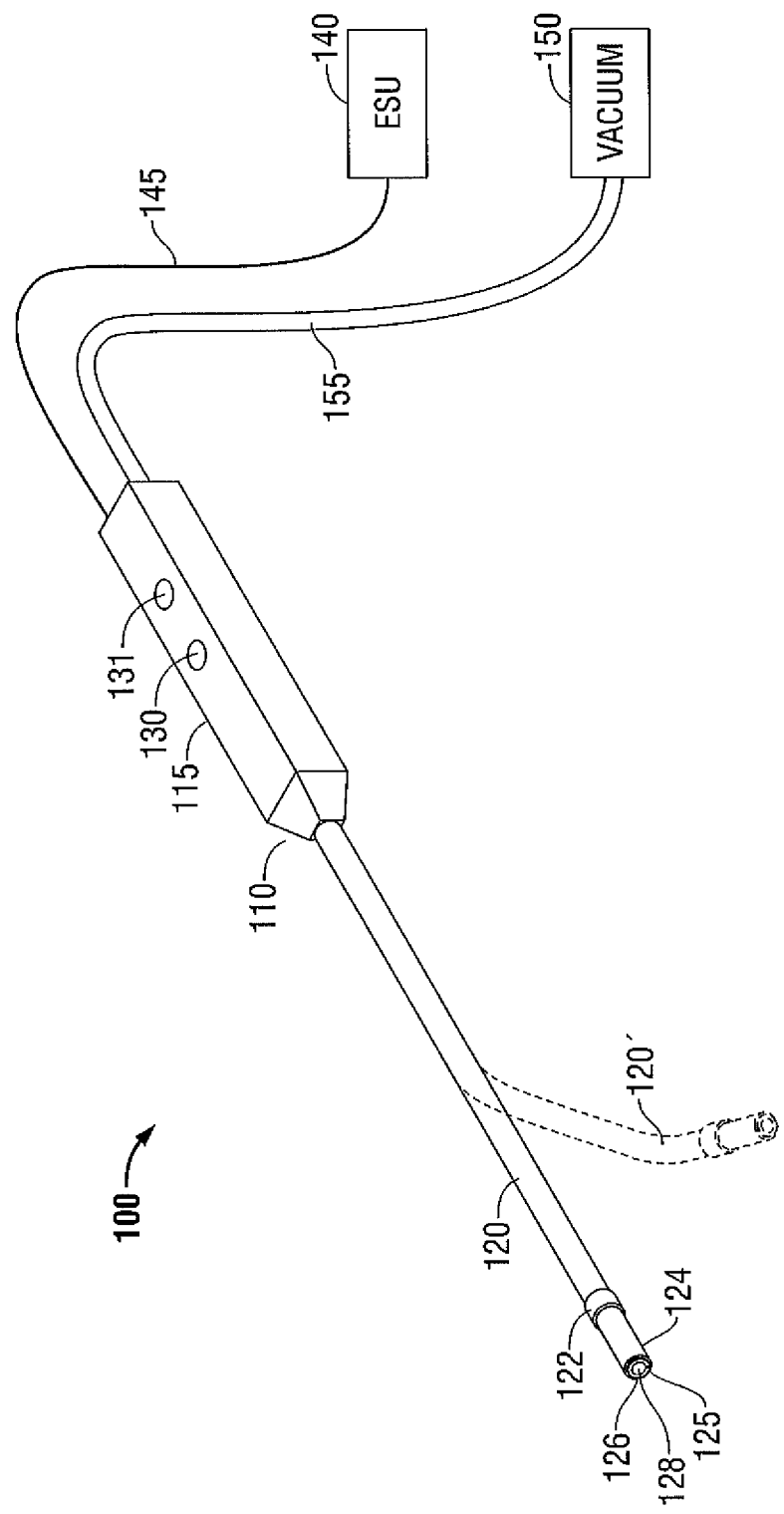
FIG. 1 is an oblique view of an embodiment of an electrosurgical suction coagulator system in accordance with the present disclosure.

Particular embodiments of the present disclosure are described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is further from the user. In the following description, wellknown functions or constructions are not described in detail to avoid obscuring the present disclosure in unnecessary detail.

With reference to FIG. 1, an electrosurgical suction coagulator system 100 is presented having a suction coagulator 110 that is operably coupled to an electrosurgical generator 140 via a conductor 145. Suction coagulator 110 is operably coupled to a vacuum source 150 by a lumen 155. Suction coagulator 110 includes a handle 115 disposed at a proximal end thereof and an elongated shaft 120 extending distally from the handle 115. Shaft 120 includes an insulating sheath 126 disposed at least partially thereon. Insulating sheath 126 is formed from any suitable dielectric material, for example, polymeric materials such as PU, PVC, and the like. The shaft 120 may be formed from material having malleable or flexible properties, for example without limitation, metallic material such as aluminum and alloys thereof. A shaft 120 thus formed may be bent to a desired shape by the user, as shown by way of example by bent shaft 120' (shown in phantom).

Shaft 120 includes a tube-like electrode 125 for delivering electrosurgical energy to tissue. The electrode 125 is disposed coaxially through shaft 120 and is exposed at a distal end 124 of shaft 120 to form an aspiration port 128 defined therethrough. Tube-like electrode 125 defines a conduit (not explicitly shown) longitudinally through shaft 120 to provide suction to a surgical site. By way of the conduit, the aspiration port 128 is in fluid communication with vacuum source 150 via lumen 155. The outer diameter of tube-like electrode 125 is sized similarly to the inner diameter of shaft 120 to form a press or interference-fit between electrode 125 and shaft 120. In use, insulating sheath 126 is configured to provide electrical insulation between electrode 125 and the surface of shaft 120.

Disposed concentrically about shaft 120 and proximal to the distal end 124 thereof is a thermally conductive member 122. The diameter of shaft 120 is accordingly sized similarly to the inner diameter of member 122 to form a press or interface-fit between member 122 and shaft 120. Alternatively or additionally, member 122 may be coupled to shaft 120 by any suitable coupling technique such as, for example, crimping, welding, soldering, adhesive, etc. During a surgical procedure, member 122 is positioned relative to shaft 120 so as to sufficiently impede the propagation of thermal energy proximally and/or away from the surgical site and/or the distal end 124 of shaft 120. To sufficiently impede proximal propagation of thermal energy, member 122 is formed of a material less thermally conductive than that of shaft 120. More specifically, tube-like electrode 125 has a first thermal conductivity $K_1$ and member 122 has a second thermal conductivity $K_2$ that is less than the thermal conductivity $K_1$ of tube-like electrode 125. For example, member 122 may be formed from a suitable thermally conductive material such as, without limitation, stainless steel, steel, polyvinyl chloride (PVC), thermoplastic polymer, etc. To electrically insulate member 122, a suitable insulating material (e.g., an insulative coating, a heat-shrink insulator, etc.) may be applied to at least a portion of the surface of member 122. Additionally or alternatively, at least a portion of member 122 may be made from a suitable non-conductive material.

In an embodiment, handle 115 includes a control 130 (e.g., handswitch) for controlling the application of electrosurgical energy, i.e., activation and deactivation of an electrosurgical signal. Handle 115 includes an additional or second control 131 for controlling the application of suction to the surgical site. In embodiments, control 131 may be operably coupled to a valve (not shown) that may be disposed within handle 115, shaft 120, vacuum source 150, and/or lumen 155. In other embodiments, control 131 may be operably coupled to a regulator, motor control, or other suitable manner of vacuum control.

Figure 2A:
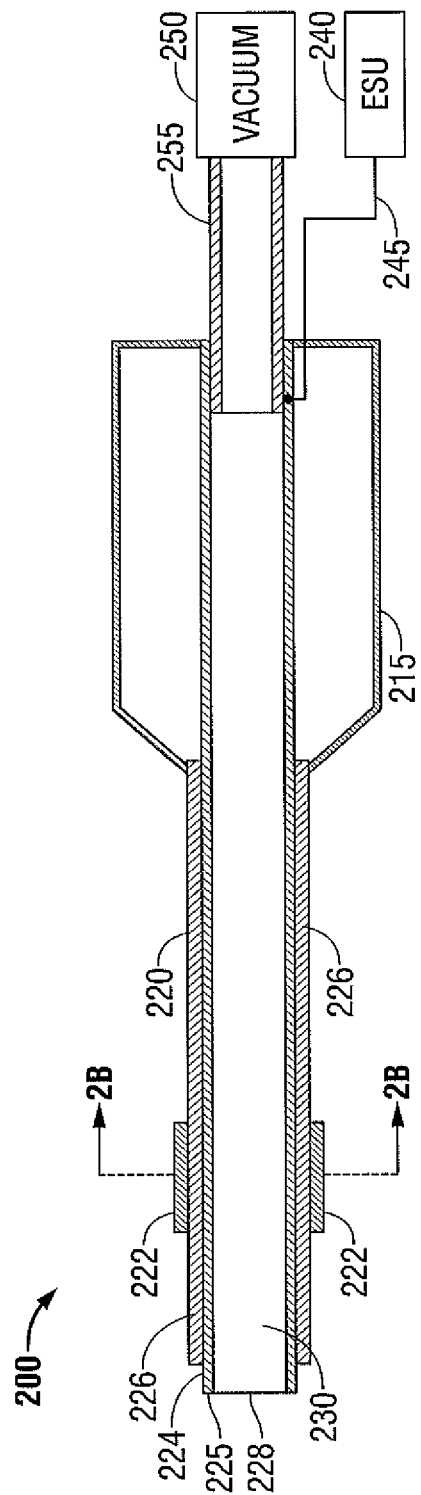
FIG. 2A is a side cutaway view of an embodiment of an electrosurgical suction coagulator in accordance with the present disclosure.
Figure 2B:
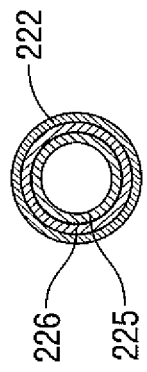
FIG. 2B is a section view of the electrosurgical suction coagulator of FIG. 2A.

Turning now to FIGS. 2A and 2B, a suction coagulator 200 in accordance with the present disclosure is operably coupled to an electrosurgical generator 240 via a conductor 245 and includes a housing 215 disposed proximally to an elongated shaft 220. Housing 215 may be a handle. Shaft 220 includes an insulating sheath 226 formed from any suitable dielectric material, for example, polymeric materials such as PU, PVC, and the like.

A tube-like electrode 225 for delivering electrosurgical energy to tissue is disposed coaxially though shaft 220 and is exposed at a distal end 224 of shaft to form an aspiration port 228 defined therethrough. Tube-like electrode 225 defines a conduit 230 longitudinally through shaft 220 to provide suction to a surgical site. Conduit 230 is in fluid communication with vacuum source 250 via lumen 255. Tube-like electrode 224 may be formed from any suitable electrically conductive material, including without limitation, aluminum or stainless steel.

A thermally conductive member 222 is disposed concentrically about shaft 220 and proximal to the distal end 224 thereof. In embodiments, thermally conductive member 222 is disposed between about 0.15 inches and about 0.25 inches from the distal end 224 of shaft 220 or disposed a suitable longitudinal distance from distal end 224 of shaft 220 such that during use of suction coagulator 220 member 222 is positioned relative to shaft 220 to efficiently impede the propagation of thermal energy proximally and/or away from the surgical site, the exposed tip of electrode 225, and/or the distal end 224 of shaft 220. In embodiments, member 222 may be between about 0.1 inches and about 0.5 inches in longitudinal length or a longitudinal length sufficient to impede the propagation of thermal energy proximally.

Figure 3A:
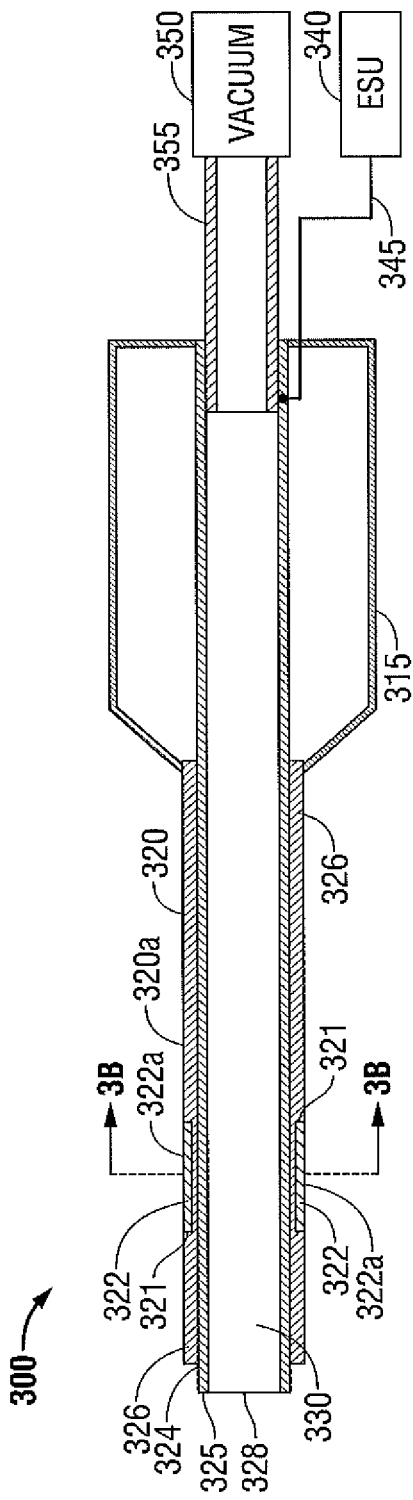
FIG. 3A is a side cutaway view of another embodiment of an electrosurgical suction coagulator in accordance with the present disclosure.
Figure 3B:
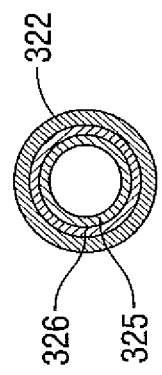
FIG. 3B is a section view of the electrosurgical suction coagulator of FIG. 3A.

Turning now to FIGS. 3A and 3B, a suction coagulator 300 in accordance with another embodiment the present disclosure is operably coupled to an electrosurgical generator 340 via a conductor 345 and includes a housing 315 disposed proximally to an elongated shaft 320. Shaft 320 includes an insulating sheath 326 formed from any suitable dielectric material.

A tube-like electrode 325 for delivering electrosurgical energy to tissue is disposed coaxially though shaft 320 and is exposed at a distal end 324 of shaft to form an aspiration port 328 defined therethrough. Tube-like electrode 325 defines a conduit 330 longitudinally through shaft 320 to provide suction to a surgical site. Conduit 330 is in fluid communication with a vacuum source 350 via a lumen 355. Tube-like electrode 325 may be formed from any suitable electrically conductive material, including without limitation, aluminum or stainless steel.

Shaft 320 includes a recess 321 formed concentrically therein and proximal to the distal end 324 thereof. A thermally conductive member 322 is disposed concentrically within the recess 321 (e.g., via welding, adhesive, etc.), such that an outer surface 322a of thermally conductive member 322 is substantially coplanar with an outer surface 320a of shaft 320 and the insulating sheath 326 is disposed between thermally conductive member 322 and tube-like electrode 325. In this scenario, the diameter of shaft 320 is substantially uniform along at least a majority along the length thereof.

In embodiments, recess 321 is disposed between about 0.15 inches and about 0.25 inches from the distal end 324 of shaft 320 or disposed a suitable distance from distal end 324 of shaft 320 such that during use of suction coagulator 300, member 322 is positioned relative to shaft 320 to efficiently impede the propagation of thermal energy proximally and/or away from the surgical site and/or the distal end 324 of shaft 320. In embodiments, member 322 may be between about 0.1 inches and about 0.5 inches in longitudinal length or a longitudinal length sufficient to impede the propagation of thermal energy proximally. The longitudinal length of recess 321 may be varied in accordance with the longitudinal length of member 322 to receive member 322 therein.

Figure 4:
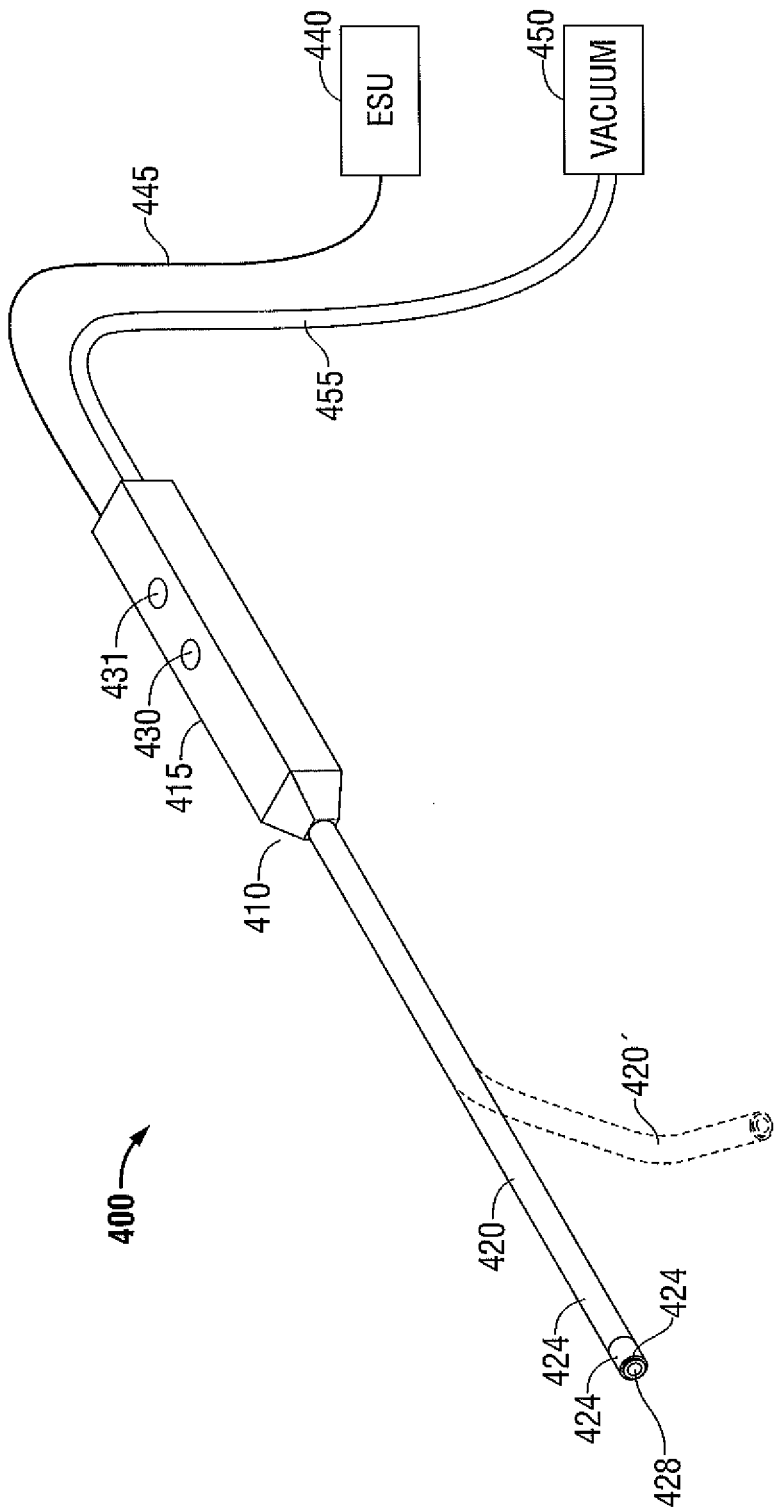
FIG. 4 is oblique view of another embodiment an electrosurgical suction coagulator system in accordance with the present disclosure.

FIG. 4 illustrates another embodiment of the presently disclosed electrosurgical coagulator system shown generally as 400. Electrosurgical coagulator system 400 is substantially as described above with respect to system 100 but includes additional features which are discussed in detail below. As with system 100, system 400 includes a suction coagulator 410 operably coupled to an electrosurgical generator 440 via a conductor 445 and to a vacuum source 450 by a lumen 455. Suction coagulator 410 includes a handle 415 disposed at a proximal end thereof and an elongated shaft 420 extending distally from the handle 415. Shaft 420 includes an insulating sheath 426 disposed at least partially thereon. Insulating sheath 426 is formed from any suitable dielectric material, for example, polymeric materials such as PU, PVC, and the like. The shaft 420 may be formed from material having malleable or flexible properties, for example without limitation, metallic material such as aluminum and alloys thereof. A shaft 420 thus formed may be bent to a desired shape by the user, as shown by way of example by bent shaft 420' (shown in phantom).

Shaft 420 includes a tube-like electrode 425 for delivering electrosurgical energy to tissue. The electrode 425 is disposed coaxially through shaft 420 and defines a conduit (not explicitly shown) longitudinally through shaft 420 to provide suction to a surgical site. An electrically conductive distal tip 422 is mechanically coupled to a distal end of the tube-like electrode 425 such that the distal tip 422 is exposed at a distal end 424 of shaft 420 to form an aspiration port 428 defined therethrough. The distal tip 422 is in electrical communication with tube-like electrode 425 to deliver electrosurgical energy to tissue during a surgical procedure. In embodiments, tube-like electrode 425 may be at least partially exposed at the distal end 425 of shaft 420. By way of the conduit (not explicitly shown), the aspiration port 428 is in fluid communication with vacuum source 450 via lumen 455. The outer diameter of tube-like electrode 425 is sized similarly to the inner diameter of shaft 420 to form a press or interference-fit between electrode 425 and shaft 420. In use, insulating sheath 426 is configured to provide electrical insulation between electrode 425 and the surface of shaft 420.

The inner diameter of the distal tip 422 is sized similarly to the outer diameter of tube-like electrode 425 to form a fit (e.g., threaded-fit, press-fit, interface-fit, etc.) between distal tip 422 and tube-like electrode 425. Additionally or alternatively, distal tip 422 may be mechanically coupled to the distal end of tube-like electrode 425 by any suitable coupling technique or combination of coupling techniques such as, for example, crimping, welding, soldering, adhesive, or any combination thereof.

To sufficiently impede proximal propagation of thermal energy, the distal tip 422 is formed of a material less thermally conductive than that of the shaft 420. For example, distal tip 422 may be formed from a suitable thermally conductive material such as, without limitation, stainless steel, steel alloy, lead, aluminum alloy, etc. In this manner, the distal tip 422 operates to sufficiently impede the propagation of thermal energy proximally and/or away from the surgical site and/or the distal end 424 of the shaft 420 during a surgical procedure.

Referring now to FIGS. 5A, 5B, and 5C, another embodiment of the suction coagulator 410 of FIG. 4 is shown generally as 500. The suction coagulator 500 is operably coupled to an electrosurgical generator 540 via a conductor 545 and includes a housing 515 disposed proximally to an elongated shaft 520. Shaft 520 includes an insulating sheath 526 formed from any suitable dielectric material, for example, polymeric materials such as PU, PVC, and the like.

A tube-like electrode 525 for delivering electrosurgical energy to tissue is disposed coaxially though shaft 520 and is exposed at a distal end 524 of shaft to form a male threaded portion 535a. An electrically conductive distal tip 522 (shown separated from tube-like electrode 525) includes a female threaded portion 535b disposed at least partially within the distal tip 522 and configured to receive male threaded portion 535a therein in a thread-fit manner to mechanically couple distal tip 522 to tube-like electrode 525 and provide electrical communication therebetween to deliver electrosurgical energy to tissue. Once mechanically coupled to tube-like electrode 525, distal tip 522 is exposed at a distal end 524 of shaft 520 to form an aspiration port 528 defined therethrough. Tube-like electrode 525 defines a conduit 530 longitudinally through shaft 520 to provide suction to a surgical site via aspiration port 528. Conduit 530 is in fluid communication with vacuum source 550 via lumen 555. Tube-like electrode 525 may be formed from any suitable electrically conductive material, including without limitation, aluminum or stainless steel. In embodiments, tube-like electrode 525 may be at least partially exposed at the distal end 525 of shaft 520.

The inner diameter of the distal tip 522 is sized similarly to the outer diameter of tube-like electrode 525 to facilitate the threading of female threaded portion 535b of distal tip 522 about male threaded portion 535a of tube-like electrode 525. Once distal tip 522 and tube-like electrode 525 are threaded together in this manner, the outer periphery of distal tip 522 may be configured to be substantially coplanar with the outer periphery of shaft 520 and/or insulating sheath 526 or, alternatively, to be substantially coplanar with the outer periphery of tube-like electrode 525.

In embodiments, distal tip 522 may be between about 0.1 inches and about 0.5 inches in longitudinal length or a longitudinal length sufficient to impede the propagation of thermal energy proximally.

Referring now to FIG. 5B, an embodiment of distal tip 522 may include a wave-like electrical conductor 560 configured to electrically communicate with tube-like electrode 525 when distal tip 522 is threaded to tube-like electrode 525 to deliver electrosurgical energy to tissue during a surgical procedure. In this embodiment, distal tip 522 includes a thermally conductive polymer or so-called "cool polymer" disposed therein to impede the propagation of thermal energy from electrical conductor 560 during a surgical procedure.

FIG. 5C shows another embodiment of distal tip 522 having a plurality of vertical electrical conductors 570 intersected by one or more horizontal electrical conductors 572. One or more of conductors 570 and 572 are in electrical communication with tube-like electrode 525 when distal tip 522 is threaded to tube-like electrode 525 to deliver electrosurgical energy to tissue during a surgical procedure. In this embodiment, distal tip 522 includes a thermally conductive polymer or so-called "cool polymer" disposed therein to impede the propagation of thermal energy from electrical conductors 570 and 572 during a surgical procedure.

Referring now to FIGS. 6A, 6B, and 6C, another embodiment of the suction coagulator 410 of FIG. 4 is shown generally as 600. The suction coagulator 600 is operably coupled to an electrosurgical generator 640 via a conductor 645 and includes a housing 615 disposed proximally to an elongated shaft 620. Shaft 620 includes an insulating sheath 626 formed from any suitable dielectric material, for example, polymeric materials such as PU, PVC, and the like.

A tube-like electrode 625 for delivering electrosurgical energy to tissue is disposed coaxially though shaft 620 and is exposed at a distal end 624 of shaft. Tube-like electrode 625 defines a conduit 630 longitudinally through shaft 620 to provide suction to a surgical site. Conduit 630 is in fluid communication with a vacuum source 650 via a lumen 655. Tube-like electrode 625 may be formed from any suitable electrically conductive material, including without limitation, aluminum or stainless steel.

Suction coagulator 600 further includes an electrically conductive distal tip 622 configured to mechanically couple to tube-like electrode 525 and provide electrical communication therebetween to deliver electrosurgical energy to tissue during a surgical procedure. Distal tip 622 may be mechanically coupled to tube-like electrode 625 by any suitable coupling technique or combination of coupling techniques such as, for example, press-fit, interface-fit, crimping, welding, soldering, adhesive, or any combination thereof. Once mechanically coupled to tube-like electrode 625, distal tip 622 is exposed at a distal end 624 of shaft 620 to form an aspiration port 628 defined therethrough. Tube-like electrode 625 defines a conduit 630 longitudinally through shaft 620 to provide suction to a surgical site via aspiration port 628. Conduit 630 is in fluid communication with vacuum source 650 via lumen 655. Tube-like electrode 625 may be formed from any suitable electrically conductive material, including without limitation, aluminum or stainless steel. In embodiments, tube-like electrode 625 may be at least partially exposed at the distal end 625 of shaft 620.

The inner diameter of the distal tip 622 is sized similarly to the outer diameter of tube-like electrode 625 to facilitate mechanical coupling of distal tip 622 to tube-like electrode 625. Once distal tip 622 is coupled to tube-like electrode 625 in this manner, the outer periphery of distal tip 622 may be configured to be substantially coplanar with the outer periphery of shaft 620 and/or insulating sheath 626 or, alternatively, to be substantially coplanar with the outer periphery of tube-like electrode 625.

In embodiments, distal tip 622 may be between about 0.1 inches and about 0.5 inches in longitudinal length or a longitudinal length sufficient to impede the propagation of thermal energy proximally.

Referring now to FIG. 6B, an embodiment of distal tip 622 may include a wave-like electrical conductor 660 configured to electrically communicate with tube-like electrode 625 when distal tip 622 is mechanically coupled to tube-like electrode 625 to deliver electrosurgical energy to tissue during a surgical procedure. In this embodiment, distal tip 622 includes a thermally conductive polymer 665 or so-called "cool polymer" disposed therein to impede the propagation of thermal energy from electrical conductor 660 during a surgical procedure.

FIG. 6C shows another embodiment of distal tip 622 having a plurality of vertical electrical conductors 670 intersected by one or more horizontal electrical conductors 672. One or more of conductors 670 and 672 are in electrical communication with tube-like electrode 625 when distal tip 622 is mechanically coupled to tube-like electrode 625 to deliver electrosurgical energy to tissue during a surgical procedure. In this embodiment, distal tip 522 includes a thermally conductive polymer or so-called "cool polymer" disposed therein to impede the propagation of thermal energy from electrical conductors 670 and 672 during a surgical procedure.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. An electrosurgical suction coagulator, comprising:
a housing having proximal and distal ends and a substantially malleable elongated tube-like shaft extending longitudinally from the distal end thereof, the elongated tube-like shaft including:
a tube-like dielectric sheath;
a tube-like electrode having a first thermal conductivity $K_1$ disposed coaxially through the tube-like dielectric sheath and configured to operably couple to a source of electrosurgical energy, wherein a distal end of the tube-like electrode protrudes at least partially from a distal end of the tube-like shaft, the tube-like electrode having at a distal end thereof at least one aspiration port defined therein, the tube-like electrode being adapted at a proximal end thereof to operably couple to a source of suction; and
a thermally conductive member having a second thermal conductivity $K_2$ that is less than $K_1$, the thermally conductive member being disposed concentrically about the tube-like shaft and substantially adjacent to the distal end thereof, the thermally conductive member being configured to impede the propagation of thermal energy in a proximal direction from the distal end of the tube-like shaft,
wherein the tube-like shaft includes a recess disposed concentrically therein substantially adjacent to the distal end thereof, the recess configured to receive the thermally conductive member therein.

2. An electrosurgical suction coagulator according to claim 1, wherein an outer surface of the thermally conductive member is substantially coplanar with an outer surface of the tube-like shaft.

3. An electrosurgical suction coagulator according to claim 1, wherein the diameter of the tube-like shaft is substantially uniform along at least a portion of the longitudinal length thereof.

4. An electrosurgical suction coagulator according to claim 1, wherein the distal end of the tube-like electrode protrudes at least partially from a distal end of the tube-like shaft.

5. An electrosurgical suction coagulator according to claim 1, wherein a longitudinal length of the thermally conductive member is between a range of about 0.1 inches and about 0.5 inches.

6. An electrosurgical suction coagulator according to claim 1, wherein the thermally conductive member includes an insulative material applied thereto.

7. An electrosurgical suction coagulator according to claim 1, wherein the thermally conductive member is made from a material selected from the group consisting of stainless steel, steel, PVC and thermoplastic polymer.

8. An electrosurgical suction coagulator according to claim 1, further comprising:

at least one control that activates at least one of the source of electrosurgical energy and the source of suction.

9. An electrosurgical suction coagulator according to claim 1, wherein the tube-like shaft is selectively deformable.

10. An electrosurgical suction coagulator according to claim 1, wherein the tube-like shaft is formed from one of aluminum, aluminum alloy, polyurethane and polyvinyl chloride.

11. An electrosurgical suction coagulator, comprising:
a housing having proximal and distal ends and a substantially malleable elongated tube-like shaft extending longitudinally from the distal end thereof, the elongated tube-like shaft including:
a tube-like dielectric sheath; and
a tube-like electrode disposed coaxially through the tube-like dielectric sheath and configured to operably couple to a source of electrosurgical energy, wherein a distal end of the tube-like electrode protrudes at least partially from a distal end of the tube-like shaft, the tube-like electrode having at a distal end thereof at least one aspiration port defined therein, the tube-like electrode being adapted at a proximal end thereof to operably couple to a source of suction;

wherein the tube-like shaft includes a recess defined concentrically therein, the recess being configured to receive a thermally conductive member therein adapted to impede the propagation of thermal energy proximally from the distal end of the tube-like shaft.

12. An electrosurgical suction coagulator according to claim 11, wherein the thermally conductive member is disposed substantially adjacent to the distal end of the tube-like shaft.

13. An electrosurgical suction coagulator according to claim 11, wherein the thermally conductive member is made from a material having less thermal conductivity than the tube-like electrode.

14. An electrosurgical suction coagulator according to claim 11, wherein an outer surface of the thermally conductive member is substantially coplanar with an outer surface of the tube-like shaft.

15. An electrosurgical suction coagulator according to claim 11, wherein the diameter of the tube-like shaft is substantially uniform along at least a portion of the longitudinal length thereof.

* * * * *